United States Patent [19]

Carlon et al.

[11] 4,343,177
[45] Aug. 10, 1982

[54] FLOW COMPENSATED GAS COMPARISON PROBE

[75] Inventors: Hugh R. Carlon, Bel Air; Bernard V. Gerber, Randallstown, both of Md.

[73] Assignee: The United States of America as represented by the Secretary of the Army, Washington, D.C.

[21] Appl. No.: 204,744

[22] Filed: Nov. 7, 1980

[51] Int. Cl.³ ............................................. G01F 13/00
[52] U.S. Cl. ........................................ 73/23; 73/1 G; 73/196
[58] Field of Search .................. 73/23, 27 R, 29, 196, 73/1 G

[56] References Cited

U.S. PATENT DOCUMENTS

| | | |
|---|---|---|
| 2,734,381 | 2/1956 | Jacobson ............................ 73/27 X |
| 3,106,088 | 10/1963 | Kieselbach ............................ 73/27 |
| 3,334,513 | 8/1967 | Thomas ............................ 73/27 |
| 3,416,357 | 12/1968 | Kelsey et al. ............................ 73/23 |
| 3,437,446 | 4/1969 | Pierce ............................ 73/27 X |
| 3,474,661 | 10/1969 | Gerdes ............................ 73/27 |
| 3,715,911 | 2/1973 | Chuan ............................ 73/23 X |

*Primary Examiner*—Herbert Goldstein
*Attorney, Agent, or Firm*—Nathan Edelberg; Robert P. Gibson; Max Yarmovsky

[57] ABSTRACT

A gas comparison probe contains first and second sensor elements isolated from each other. Air is drawn across a surface to be monitored and directed onto the first sensor element. Air is drawn from a location spaced away from the surface to be monitored and directed onto the second sensor element. A flow constrictor in the air flow path to one of the sensor elements is used to calibrate the outputs of the two sensor elements under known conditions before attempting to monitor air flow which may contain a gas to be detected.

12 Claims, 1 Drawing Figure

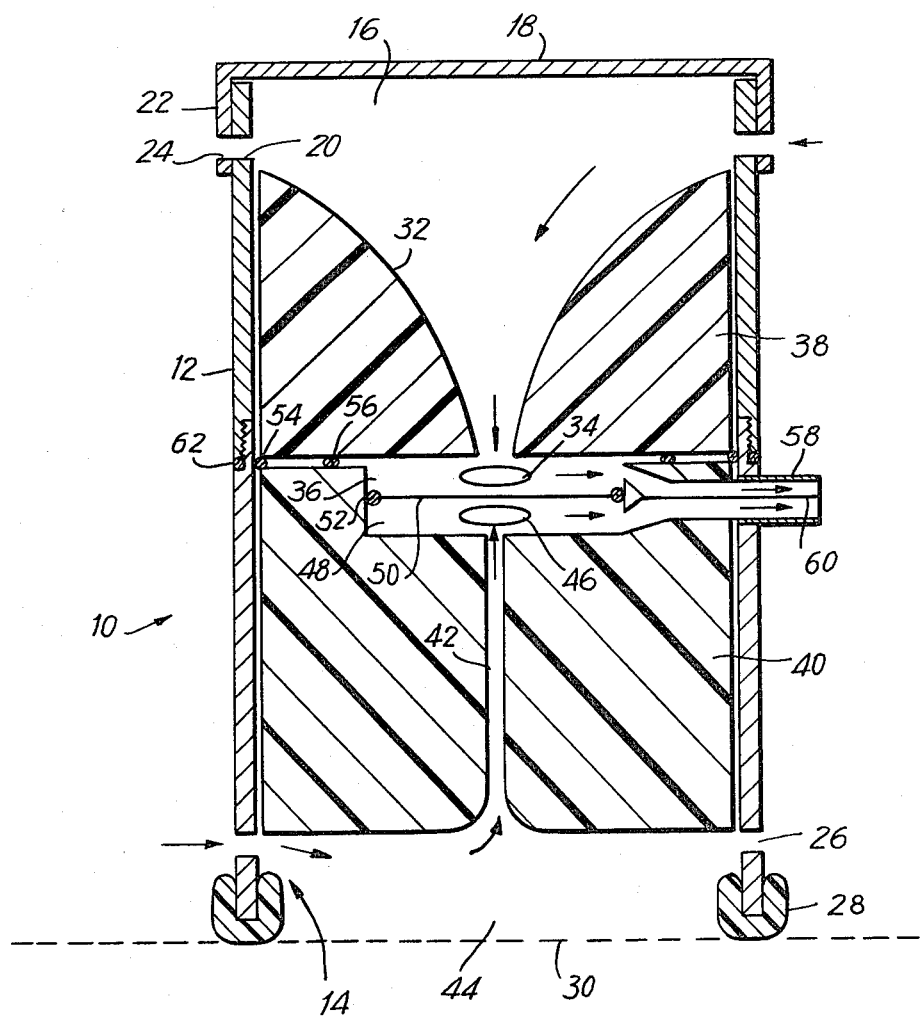

FLOW COMPENSATED GAS COMPARISON PROBE

GOVERNMENTAL INTEREST

The invention described herein may be manufactured, used and licensed by or for the Government for governmental purposes without the payment to us of any royalties thereon.

BACKGROUND OF THE INVENTION

The present invention relates to gas probes and more particularly to gas probes for sampling gases and vapors evolved from, or closely adjacent to, surfaces.

In order to sample gases evolved from, or closely adjacent to, potentially contaminated surfaces, detectors have been used which included a gas probe consisting essentially of an inverted funnel placed over the surface and a vacuum pump to draw air from around a perimeter of the funnel and into a detector. A cannister of activated charcoal was occasionally employed to purify the ambient air before permitting it to be drawn over the surface to remove interfering components from the gas.

The above method was limited in its sensitivity due to the effect of air temperature, humidity and environmental trace elements in the air. The presence of such elements changed the sensitivity of the detector and contributed errors to the measurement.

OBJECTS AND SUMMARY OF THE INVENTION

Accordingly, it is an object of the present invention to provide a gas probe which overcomes the drawbacks of the prior art.

It is a further object of the invention to provide a gas comparison probe which permits drawing gas in one stream over an environmental surface and onto a gas sensor element while simultaneously drawing gas in a second stream originating remote from the surface onto a second gas sensor element.

It is a further object of the invention to provide means for compensating the gas flow to the two sensor elements to calibrate them in the absence of a gas to be measured whereby environmental effects of temperature, humidity and trace gases may be cancelled out in a comparison of the outputs of the two sensor elements.

Accordingly, it is an aspect of the invention to provide a gas probe for sensing a characteristic of a gas near a surface comprising a first chamber, a first gas sensor in the first chamber, means for drawing a first flow of gas across the surface and impinging the first flow on the first gas sensor, a second chamber, a second gas sensor in the second chamber, means for drawing a second flow of gas originating a substantial distance from the surface and impinging the second flow on the second gas sensor, means for isolating the first and second flows, and means for independently varying at least one of the first and second flows whereby outputs of the first and second gas sensors may be calibrated.

Accordingly, it is a feature of the present invention to provide a gas probe for comparing a characteristic of first and second flows of gas originating in first and second spaced-apart locations respectively, comprising a housing, means for admitting the first flow of gas to the housing, a first well in the housing, a first sensor in the first well, means for impinging the first flow on the first sensor, a second well in the housing isolated from the first well, a second sensor in the second well, means for impinging the second flow on the second sensor, the first and second sensors being sensitive to a characteristic of the first and second flows, and means for controlling the ratio of the first and second flows.

The above, and other objects, features and advantages of the present invention will become apparent from the following description read in conjunction with the accompanying drawings, in which like reference numerals designate the same elements.

BRIEF DESCRIPTION OF THE DRAWING

The FIGURE shows a longitudinal cross section of a flow compensating gas comparison probe according to an embodiment of the present invention.

DETAILED DESCRIPTION OF THE PREFERRED EMBODIMENT

Referring now to the FIGURE, a gas comparison probe, shown generally at 10, includes a generally cylindrical housing 12 having an open bottom 14 and a top 16 which is closed by a cover 18.

The perimeter of top 16 is pierced by a plurality of spaced apart holes 20. A depending lip 22 includes a plurality of spaced apart holes 24 whose spacing matches the spacing of holes 20. By rotating cover 18 with respect to housing 12, holes 24 can be made to align with holes 20 to permit relatively unrestricted flow of air into top 16 or holes 24 and 20 can be partially or completely misaligned to provide any amount of constriction to air flow which is desired.

The perimeter of bottom 14 is pierced with a plurality of holes 26. The lower extremity of bottom 14 includes a sealing ring such as, for example, a foam rubber gasket 28 which can be pressed against a generally planar surface 30 to be monitored.

An upper flow-directing surface 32 provides a generally conical flow path for directing a flow of air indicated by arrows onto a sensor element 34 in an upper well 36. Flow-directing surface 32 may be formed by a sheet metal or other thin material but is preferably formed as a conical opening in a solid block of material 38 which may be of any convenient material such as metal or plastic.

A lower block of material 40 includes a central flow channel 42 therein leading from a relatively flat gas flow chamber 44 and effective to direct a flow of air and gas from holes 26 in the direction indicated by arrows and to impact the air on a sensor element 46 in a lower well 48. Upper well 36 and lower well 48 are isolated from each other by a septum 50 which is sealed against gas flow at the edges thereof by a resilient member 52. Gas flow around the edges of blocks 38 and 40 is prevented by sealing members such as, for example, O-rings 54 and 56.

A nipple 58 is connected through housing 12 to upper and lower wells 36 and 48. A septum 60 in nipple 58 may be employed to maintain separate gas flows through nipple 58 from upper and lower wells 36 and 48 to an external detector (not shown) where the gas content of the separate flows may be detected. A vacuum pump (not shown) attached to nipple 58 or associated with the external detector (not shown) draws the air and gas along the flow paths shown by arrows.

Housing 12 may conveniently be separated into upper and lower halves at a threaded connection 62 to permit access to sensor elements 34 and 46 as well as to septum 50. It is within the contemplation of the present invention that a replaceable unit including sensor elements 34 and 46, septum 50 and sealing member 52 may be provided and that these elements may plug in to the cavity defined by upper and lower wells 36 and 48 to change the characteristics of the probe. Electrical connection to sensor elements 34 and 46 may be by conventional means such as, for example, by wiping contacts (not shown) of a conventional type.

Sensor elements 34 and 46 may be of any convenient type for either equalizing the gas flow along the two flow paths or for actually sensing a characteristic or component of the gas in the two flow paths. For example, if sensor elements 34 and 46 are thermistors, they may be used to equalize the flow of gas mass in the two flow channels. The thermistors are heated by an externally applied voltage and are cooled in proportion to the mass of gas flowing over them. By externally measuring the resistance of thermistors in sensor elements 34 and 46, a measure of the thermistor temperatures and the amount of gas flow in the two channels is provided. Cover 18 may then be rotated to change the alignment between holes 24 and 20 while observing the resistance of thermistors in sensor elements 34 and 46 until their resistances are equal. At this point, equal gas flow is obtained in the two channels. Thus, a detector (not shown) connected to nipple 58 receives equal quantities of gas in the two flow channels. The air flowing through holes 26 and across surface 30 in gas flow chamber 44 will pick up any volatile gases from surface 30 aided by the slightly reduced pressure produced by the suction drawing the gases toward nipple 58.

The air directed to sensor elements 34 and 46 should have about the same temperature, humidity and trace components as are present in the ambient air and, if the flow is properly calibrated, any differences in the two air flows measured by the external detector (not shown) should be due to evolved gases from surface 30. If sensor elements 34 and 46 are employed in an electrical or electronic bridge circuit, very sensitive measurements of flow or other differences may be obtained.

Sensor elements 34 and 46, instead of being purely flow-type measurement devices, may instead be sensitive to gas composition. For example, sensor elements 34 and 46 may be sensitive to humidity or to the partial pressure of particular gases therein. They may change their electrical characteristics according to the gas composition whereby external circuits (not shown) may be employed to compare the outputs of the two sensors for a direct measurement of the difference between the gas passed across surface 30 and that drawn through holes 24 and 20 a substantial distance away from surface 30. Gas comparison probe 10 may be initially calibrated by substituting a surface in place of surface 30 which has known characteristics. For example, a cover (not shown) may be included over open end 14 for calibration purposes. The cover prevents direct gas flow through open end 14 and forces gas to flow through openings 26. Since the characteristics of the cover are known, rotational adjustment of cover 18 can be used to equalize the outputs of sensor elements 34 and 46 so that, when gas comparison probe is applied to a surface 30 to be monitored, any difference between the outputs of sensor elements 34 and 46 may be considered due to the presence of evolved gases from surface 30.

Although any suitable devices may be employed in sensor elements 34 and 46, coated piezoelectric crystal detectors consisting of quartz plates which are preferably cut and coated with a film of material suitable for sorbing a gas to be detected are preferred. The resonent frequency of a cut quartz crystal is sufficiently variable with mass that detection of gas differences down to parts per billion is possible.

Gas detection employing quartz crystal detectors is reported in Analytical Chemistry, Volume 49, No. 13 published on November, 1977.

When sensor elements 34 and 46 are employed for sensing the composition of gases, there may be no need for separating the flow of gas by septum 60 through nipple 58. Instead, it may only be necessary to connect a vacuum pump directly to nipple 58.

A compact gas sensing apparatus may include a gas comparison probe 10 with crystal detectors for sensor elements 34 and 46 and with the required electronics and vacuum pump attached thereto such as, for example, atop cover 18.

Having described specific embodiments of the invention with respect to the accompanying drawings, it is to be understood that the invention is not limited to those precise embodiments, and that various changes and modifications may be effected therein by one skilled in the art without departing from the scope or spirit of the invention as defined in the appended claims.

What is claimed is:

1. A gas probe for sensing a characteristic of a gas near a planar surface comprising:
   a first well chamber;
   a first gas sensor operatively disposed in said first well chamber;
   means for drawing a first flow of gas across said planar surface and impinging said first flow of gas on said first gas sensor which includes;
      a cylindrical hoising having a bottom section threadably connected to an upper section;
      a lower block member having a central channel disposed in said bottom section, said central channel communicating with a gas flow chamber adjacent to said planar surface and with said first well chamber;
   a second well chamber;
   a second gas sensor operatively disposed in said second well chamber;
   means for drawing a second flow of gas originating at a substantial distance from said planar surface and impinging said second flow of gas on said second gas sensor, which includes;
      an upper block member operatively disposed in said upper section of said housing, having a venturi shaped upper flow directing surface which permits said second flow of gas to communicate with said second well chamber;
   means for isolating said first and second flows of gas, which includes;
      a nipple member transversly disposed through a wall of said housing and positioned intermediate said lower section and said upper section of said housing, further including;
      a first septum member longitudinally disposed in said nipple member for isolating said first and second flows of gas from each other;
      second septum means operatively disposed intermediate said lower and upper section members cooperating with said first septum member for pneumatically isolating said first and second gas sensors; and means for independently varying at least one of said first and second flows of gas whereby outputs of said first and second gas sensors may be calibrated.

2. A gas probe according to claim 1 wherein said first and second gas sensors are thermistors.

3. A gas probe according to claim 2 wherein said first and second gas sensors are piezoelectric crystal detectors effective to vary their resonant frequencies through sorbtion of a predetermined gas.

4. A gas probe according to claim 1 wherein said first and second gas sensors are effective to vary an electrical characteristic thereof in response to a rate of flow.

5. A gas probe according to claim 1 wherein said first and second gas sensors are effective to change a characteristic thereof in response to a composition of gas in said first and second flows.

6. A gas probe according to claim 1 further comprising means for isolating said first and second flows of gas after impingement thereof on said first and second gas sensors.

7. A gas probe for comparing a characteristic of first and second flows of gas originating in first and second spaced-apart locations respectively, comprising;
a housing;
means for admitting said first flow of gas to said housing including;
a tubular shaped housing having a plurality of equally spaced holes disposed through the housing walls; and
pliant seal means connected to the bottom open end of said housing for interfacing between said housing and a planar surface being sampled;
a first well in said housing;
a first sensor in said first well;
means for impinging said first flow of gas on said first sensor which includes;
a lower flow block member having a central channel operatively disposed in the lower section of said housing, said central channel communicating with said first spaced-apart location and said first well;
a second well in said housing isolated from said first well;
a second sensor in said second well;
means for impinging said second flow on said second sensor which includes;
an upper flow block member having a venturi shaped orifice communicating with said second sensor;
septum means disposed intermediate said lower and upper flow block members for isolating said first and second gas flows from each other; and
a first plurality of equally spaced holes disposed in the upper end of said housing;
said first and second sensors being sensitive to a characteristic of said first and second flows of gas; and
means for controlling the ratio of said first and second flows of gas sampled by said gas probe.

8. A gas probe according to claim 7 wherein said characteristic is a rate of flow.

9. A gas probe according to claim 7 wherein said characteristic is a gas composition.

10. A gas probe according to claim 7 wherein said characteristic is a humidity.

11. A gas probe as recited in claim 1 wherein said means of independently varying at least one of said first and second flows of gas include:
a first plurality of equally spaced holes peripherally disposed through the wall of said upper section of said housing; and
a cover having a lip thereon which has a second plurality of equally spaced holes in alignment with said first plurality of holes, said cover rotationally moveable with respect to said housing to enable equalization of the outputs of said first and second gas sensors.

12. A gas probe as recited in claim 7 wherein said means for controlling the ratio of said first and second flows of gas which includes:
cover means, having a second plurality of holes therein in axial alignment with said first plurality of holes in said upper end of said housing, for regulating the relative open flow area between said first plurality of holes in said housing and said second plurality of holes in said cover means.

* * * * *